United States Patent [19]

Jensen et al.

[11] Patent Number: 5,224,389
[45] Date of Patent: Jul. 6, 1993

[54] METHOD AND APPARATUS FOR TAKING SAMPLES FROM A GROUNDWATER MONITORING SITE

[75] Inventors: Niels D. Jensen; Jorgen Christensen, both of Bjerringbro, Denmark; Konrad Gries, Hohenhameln; Hans-Joachim Jordan, Peine, both of Fed. Rep. of Germany

[73] Assignees: Grundfos International A/S, Bjerringbro, Denmark; Preussag Aktiengesellschaft, Hanover, Fed. Rep. of Germany

[21] Appl. No.: 602,340

[22] PCT Filed: Apr. 2, 1990

[86] PCT No.: PCT/DE90/00260

§ 371 Date: Dec. 5, 1990

§ 102(e) Date: Dec. 5, 1990

[87] PCT Pub. No.: WO90/12305

PCT Pub. Date: Oct. 18, 1990

[30] Foreign Application Priority Data

Apr. 7, 1989 [DE] Fed. Rep. of Germany ....... 3911366

[51] Int. Cl.⁵ .............................................. G01N 1/14
[52] U.S. Cl. .............................. 73/863.01; 73/864.34; 166/250; 166/264; 166/68; 166/72; 417/44
[58] Field of Search ............... 73/864.34, 863.01, 155, 73/864.35; 166/53, 250, 284, 68, 72, 105; 417/44, 279; 210/87, 99, 103, 739, 796, 779

[56] References Cited

U.S. PATENT DOCUMENTS

| | | | |
|---|---|---|---|
| 3,568,771 | 3/1971 | Vincent et al. | 166/53 X |
| 4,252,020 | 2/1981 | Ongley | 73/863.21 |
| 4,489,779 | 12/1984 | Dickinson et al. | 73/864.34 X |
| 4,495,991 | 1/1985 | Reijonen | 166/105 X |
| 4,585,060 | 4/1986 | Bernardin et al. | 73/864.34 X |
| 4,669,536 | 6/1987 | Ames et al. | 166/68 |
| 4,683,761 | 8/1987 | Stock | 73/864.34 |
| 4,727,936 | 3/1988 | Mioduszewski et al. | 166/53 |
| 4,961,689 | 10/1990 | Avramidis | 417/118 |
| 5,028,213 | 7/1991 | Dickinson et al. | 417/118 |

FOREIGN PATENT DOCUMENTS

| | | |
|---|---|---|
| 3820005 | 3/1972 | Fed. Rep. of Germany . |
| 146855 | 4/1981 | Fed. Rep. of Germany . |
| 216318 | 4/1981 | Fed. Rep. of Germany . |
| 3012294 | 2/1982 | Fed. Rep. of Germany . |
| 3642727 | 11/1985 | Fed. Rep. of Germany . |

*Primary Examiner*—Hezron E. Williams
*Assistant Examiner*—Michael Brock
*Attorney, Agent, or Firm*—Herbert Dubno

[57] ABSTRACT

A method for taking samples from a groundwater monitoring site realized by measuring an electric conductivity of contaminated groundwater during operating a pump at high r.p.m. and by controlling a predetermined minimum variation of the electric conductivity over a predetermined period of time with subsequent operating of the pump at low r.p.m.

8 Claims, 1 Drawing Sheet

METHOD AND APPARATUS FOR TAKING SAMPLES FROM A GROUNDWATER MONITORING SITE

CROSS REFERENCE TO RELATED APPLICATIONS

This application is a national phase application of PCT/DE 90/00260 filed 2 Apr. 1990 and based, in turn, upon German application P 39 11 366.3 filed 7 Apr. 1989.

1. Field of the Invention

This invention relates to a method for taking samples from a groundwater monitoring site, using a pump adapted to be lowered into the well of the groundwater monitoring site, and an apparatus for implementing this method.

2. Background of the Invention

It is particularly useful in areas of water procurement plants where a plurality of groundwater monitoring sites, also referred to as groundwater observation wells, are provided. They serve the function of observing the groundwater level and taking water samples which are subsequently analyzed to provide information on the quality and purity of the groundwater. As a rule, the groundwater monitoring sites comprise a well which is sunk into the water bearing stratum to be observed and includes a piping with a length of filter for the inflow of groundwater. The water samples are conveyed through the piping by means of a pump which has to be lowered in the piping at groundwater levels below the maximum suction head. In view of the conventionally small diameters of the piping of the monitoring sites, the volumetric output of the pumps for the withdrawal of samples is selected as large as possible in order to be able to purge the monitoring site prior to the taking of samples within the shortest possible time, purging involving an exchange of the groundwater that has collected at the monitoring site. To obtain the water sample, the required amount of the sample is diverted from the fluid displaced by the pump through a bypass. However, this results in the disadvantage that the sample may be contaminated as a result of the high delivery. If pumps with a lower volumetric output are used, the purging cycle of the monitoring site which precedes the sampling cycle is too time-consuming.

OBJECT OF THE INVENTION

It is an object of the present invention to provide a method of the type initially referred to which permits withdrawing of groundwater samples as free from contamination as possible with little expenditure of time and material.

Another object of the present invention is to provide an apparatus implementing the method according to the invention.

SUMMARY OF THE INVENTION

To accomplish this object, the method of the present invention provides for operation of the pump initially at high RPM or at a high frequency to obtain a high volumetric output adapted to the rate of inflow of the groundwater monitoring site and, following purging of the groundwater monitoring site, at lower RPM or at a lower frequency for the delivery of a substantially non-contaminated groundwater sample.

In a first step, the method of the invention makes possible for the groundwater monitoring site be purged in a short time in order to provide the prerequisites for the obtainment of an unadulterated water sample. A second step then involves the pumping up of the water sample without involving a change of the equipment installed, at a delivery rate reduced to such an extent as to avoid that the water pumped up is altered, for example, by degassing or the entrainment of deposits.

In one embodiment, the method of the invention involves the further steps of sensing and monitoring, during the purging cycle, a measured value characteristic of the groundwater quality and of initiating the sampling cycle after a predetermined minimum variation of this measured value is determined over a predetermined period of time. In this manner, the purging cycle is reliably prevented from being terminated prematurely or lasting unnecessarily long. According to the invention, the conductivity of the groundwater may serve as the characteristic value measured.

The apparatus includes according to the invention an electrically driven pump means suitable for installation in the piping of the groundwater monitoring site and adapted to have its RPM controlled by a controllable frequency converter provided outside the monitoring site. In accordance with the invention, the frequency converter, in combination with an independent power supply unit, is part of a mobile unit for holding and transporting water samples.

The apparatus of the invention enables the two operating modes of the method of the invention to be accomplished in an optimum manner. Thus, the speed of the frequency-controlled pump means is variable to adapt to the prevailing operating conditions. Accordingly, the quantity delivered by the pump is adjustable to the conditions prevailing at the site, both when purging the monitoring site and when pumping up the water sample. With this construction therefore, the pump is suited to adapting to the small internal diameter of the piping of the monitoring sites, permitting a sufficiently high delivery rate where pipes with diameters of 50 millimeters are used. A centrifugal type of the pump is preferable.

The pump means may be carried along with a mobile unit and lowered into the monitoring site prior to the sample being taken, or alternatively, in accordance with a further proposal of the invention, it may be a permanently installed part of a groundwater monitoring site. When taking samples, in this proposal it is only necessary to connect the pump means to the frequency converter of the mobile unit and operate it according to the method of the invention. The need to spend time on the insertion and removal of the pump means or on the rinsing of the pump means and the discharge conduit in the period between individual samples is thus obviated.

In accordance with the invention, the mobile unit also includes a measuring device for sensing and monitoring a measured value characteristic of the composition of the groundwater.

The apparatus of the invention is further suitable for equipping stationary measuring stations with two or more groundwater monitoring sites. According to the invention, each groundwater monitoring site is equipped with a pump means, and a frequency converter is adapted to be selectively connected to a respective one of the pump means. In this manner, samples can be obtained at several groundwater monitoring sites from a single measuring station, with little constructional expenditure being involved.

To simplify the apparatus of the invention and to facilitate its handling and assembly, in a further proposal of the invention the electrical lines connecting the pump means and the frequency converter may be routed in a separate duct integrally formed with the discharge conduit of the pump means. In this arrangement, the discharge conduit is suitably made of a material which is chemically neutral with respect to groundwater and its substances, preferably polytetrafluoroethylene.

If the electrical lines connecting the pump means and the frequency converter run freely in the piping of the groundwater monitoring site, the invention provides for sheathing of the lines with a material which is chemically neutral with respect to the water and its substances, particularly polytetrafluoroethylene.

BRIEF DESCRIPTION OF THE DRAWING

The above and other objects, features and advantages of our invention will become more readily apparent from the following description, reference being made to the accompanying highly diagrammatic drawing in which.

SPECIFIC DESCRIPTION

Figure 1:
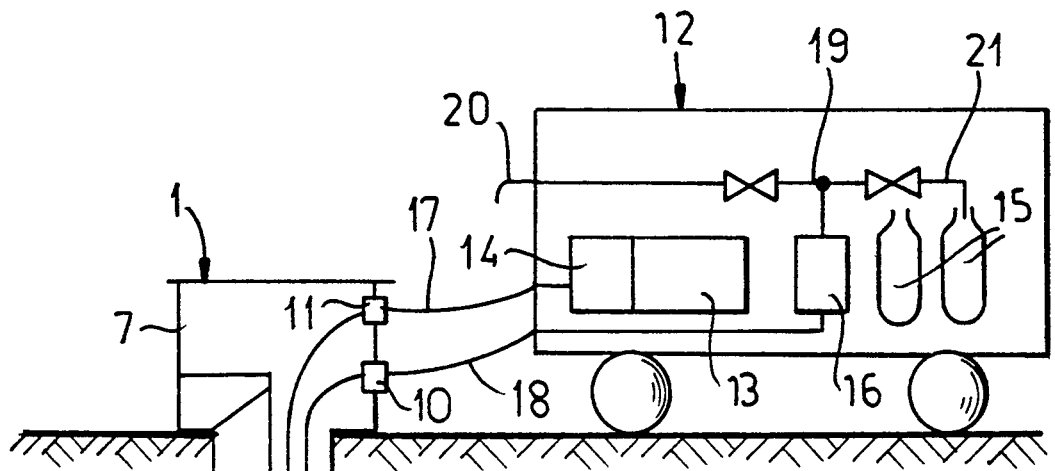
FIG. 1 illustrates schematically an apparatus of the invention as used at a groundwater monitoring site.

The groundwater monitoring site 1 illustrated is lined with a piping 2 having at its bottom end a filter 3 through which groundwater is admitted in the interior of the piping 2. Provided in the piping 2 below the groundwater level 4 is a submergible pump means 5 suspended by a cable 6 from the wellhead 7 of the groundwater monitoring site 1. The pump means 5 comprises a two-step centrifugal pump which is driven by an asynchronous squirrel-cage motor. A discharge conduit 8 and electrical lines 9 connect the pump means 5 to the wellhead 7, with the end of the discharge conduit 8 being coupled to a fitting 10 and the ends of the electrical lines 9 being coupled to a plug connector 11.

Adjacent to the wellhead 7 of the groundwater monitoring site 1 is a vehicle 12 comprising a generator 13 driven by an internal combustion engine, a controllable frequency converter 14 connected to the generator 13, a vessel 15 for receiving water samples, and a measuring device 16. Lines 17 connect the frequency converter 14 detachably to the electrical lines 9 through the plug connector 11. Connected to the fitting 10 is a conduit 18 leading via the measuring device 16 to a distributor 19 conveying the pumped up water either to a drain pipe 20 or, through a filling conduit 21, to the sample collection vessels 15.

With the apparatus described, water samples can be obtained simply and economically applying the method disclosed in the invention. The vehicle is parked at a groundwater monitoring site 1 as illustrated and hooked up to the wellhead 7 by means of the lines 17 and the conduit 18. After the generator 13 is started, the pump means is driven via the frequency converter 14 at a high frequency, purging the groundwater monitoring site at a high volumetric output. As this occurs, the electric conductivity of the water delivered is observed by the measuring device 16 in order to be able to detect variations of the groundwater quality during the purging cycle. If the conductivity measured remains constant over a predetermined period of time or within a specific variation, the purging cycle will be terminated. During purging, the water is discharged through the drain pipe 20.

For the withdrawal of water samples, the frequency of the supply voltage for the pump means is reduced such that the delivery rate drops to one liter per minute or even less. When the water delivered at such a low rate finally reaches the distributor 19, the drain pipe 20 will be shut off and the sample collection vessels 15 will be filled through the filling conduit 21. Upon completion of the filling cycle, the lines 17 and the conduit 18 will be disconnected whereupon the vehicle 12 can be moved to another groundwater monitoring site for the withdrawal of new samples.

Figure 2:
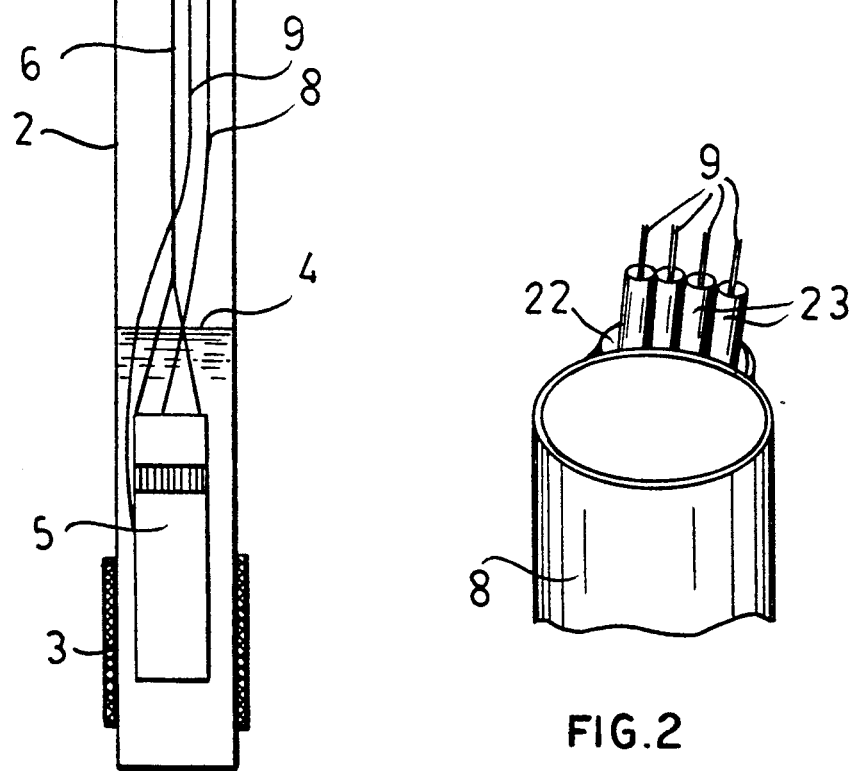
FIG. 2 is a perspective view of a discharge conduit according to the invention.

FIG. 2 is a sectional view, in perspective, of an embodiment of the discharge conduit 8 having integrally formed therewith a duct 22 with a cross section shaped in the manner of the sector of an annulus. The duct 22 holds the electrical lines 9 which inside the duct 22 are enclosed with an insulating sheath 23.

We claim:

1. A method for taking samples from a groundwater monitoring site, said method comprising the steps of:
    (a) purging a groundwater monitoring site receiving a groundwater penetrating therein at a rate of inflow by:
        ($a_1$) operating a pump adapted to be lowered into said monitoring site at a given high RPM, obtaining thereby a high volumetric output relative to said rate of inflow,
        ($a_2$) during operating of said pump at said given high RPM in step ($a_1$) measuring an electric conductivity of said groundwater;
        ($a_3$) determining a predetermined minimum variation of said electric conductivity over a predetermined period of time; and
    (b) upon determining said minimum variation over said predetermined period of time in step ($a_3$) operating said pump at a given low RPM, delivering thereby a substantially noncontaminated sample of said groundwater.

2. The method defined in claim 1 wherein the RPM of said pump is controlled by a frequency converter.

3. A groundwater sampling apparatus for taking groundwater samples, said apparatus comprising:
    at least one monitoring site receiving a groundwater penetrating therein at a rate of inflow;
    a variable speed pump adapted to be submerged in the groundwater within said site for purging thereof and delivering samples of said groundwater from the site;
    a mobile unit for holding and transporting samples of said groundwater outside said site, said mobile unit comprising:
        a controllable frequency converter operatively connected with and adapted to vary a RPM output of said pump,
        an independent electric power supply unit electrically connected with said frequency converter,
        measuring means operatively connected with said pump for measuring an electric conductivity of said samples,
        controlling means for determining a predetermined minimum variation of said electric conductivity over a predetermined period of time, and
        wire means connecting said measuring means with said frequency converter for adjusting said RPM output of said pump from an initial high RPM relative to said rate of inflow to a low RPM upon determining said minimum variation of said electric conductivity over said predetermined period of time.

4. The apparatus as claimed in claim 3, characterized in that the pump is a permanently installed part of a groundwater monitoring site.

5. The apparatus as claimed in claim 3, characterized in that the independent electric power supply unit is a generating unit driven by an internal combustion engine.

6. The apparatus defined in claim 3, further comprising:

another monitoring site receiving a respective variable speed pump; and means for selectively connecting said frequency converter to a respective one of said pumps.

7. The apparatus defined in claim 3 wherein said pump is formed with a discharge conduit provided in said site receiving said groundwater and connected with said measuring means, said wire means being electrical lines, said lines being routed in a separate duct formed integrally with said discharge conduit.

8. The apparatus defined in claim 7 wherein said site receives a pipe, said electrical lines run freely in said pipe and being provided with a sheathing, said sheathing and said discharge conduit being made of material, said material being chemically neutral with respect to said groundwater and its substances including polytetrafluoroethylene.

* * * * *